United States Patent [19]

Swenson

[11] Patent Number: 5,021,111
[45] Date of Patent: Jun. 4, 1991

[54] APPARATUS AND METHOD FOR APPLYING HEAT-SENSITIVE ADHESIVE TAPE TO A WEB MOVING AT HIGH SPEED

[75] Inventor: Douglas A. Swenson, Maplewood, Minn.

[73] Assignee: Minnesota Mining and Manufacturing Company, St. Paul, Minn.

[21] Appl. No.: 238,568

[22] Filed: Aug. 31, 1988

[51] Int. Cl.⁵ .......................... B32B 31/10; B65C 9/25
[52] U.S. Cl. ..................................... 156/264; 156/285; 156/320; 156/499; 156/568; 156/519; 156/521; 156/DIG. 36; 156/567
[58] Field of Search ............... 156/519, 521, 568, 450, 156/252, 320, DIG. 36, 264, 497, 499, 285, 567, 164, 309.9, 322; 29/121.8

[56] References Cited

U.S. PATENT DOCUMENTS

| | | | |
|---|---|---|---|
| 2,289,336 | 7/1942 | Bamford | 93/36 |
| 2,489,837 | 11/1949 | Von Hofe | 156/289 |
| 2,525,741 | 10/1950 | Von Hofe et al. | 156/215 |
| 2,613,007 | 10/1952 | Von Hofe | 156/282 |
| 2,621,823 | 12/1952 | Perry | 156/215 |
| 2,878,953 | 3/1959 | Mitchell | 156/364 |
| 2,958,437 | 11/1960 | Mengis | 216/25 |
| 2,990,081 | 6/1961 | De Neui et al. | 156/519 |
| 3,012,481 | 12/1961 | Hughes | 93/1 |
| 3,616,027 | 10/1971 | Honsel | 156/265 |
| 3,829,343 | 8/1974 | Remmert | 156/309.9 X |
| 3,850,724 | 11/1974 | Lehmacher | 156/201 |
| 3,897,293 | 7/1975 | Babcock | 156/568 |
| 3,933,564 | 1/1976 | Jensen | 156/265 |
| 3,957,570 | 5/1976 | Helm | 156/519 |
| 3,963,557 | 6/1976 | Patterson | 156/519 |
| 4,019,948 | 4/1977 | Hudalla et al. | 156/519 |
| 4,061,527 | 12/1977 | Traise | 156/519 |
| 4,200,389 | 4/1980 | Matsui et al. | 29/121.8 |
| 4,333,786 | 6/1982 | Civardi et al. | 156/309.9 X |
| 4,339,292 | 7/1982 | Itoh et al. | 156/322 X |
| 4,358,336 | 11/1982 | Focke et al. | 156/518 |
| 4,412,879 | 11/1983 | Ottaviano | 156/145 |
| 4,427,474 | 1/1984 | Ottaviano | 156/145 |
| 4,475,969 | 10/1984 | Reed | 156/152 |
| 4,481,067 | 11/1984 | Off et al. | 156/541 |
| 4,576,669 | 3/1986 | Caputo | 156/145 |
| 4,642,085 | 2/1987 | Helm | 493/222 |
| 4,662,965 | 5/1987 | DiFrank et al. | 156/215 |
| 4,710,190 | 12/1987 | Wood et al. | 604/389 |
| 4,726,876 | 2/1988 | Tomsovic, Jr. | 156/552 |
| 4,743,334 | 5/1988 | Singer | 156/582 |
| 4,795,510 | 1/1989 | Wittrock et al. | 156/64 |
| 4,822,437 | 4/1989 | Bryniarski et al. | 156/519 X |

FOREIGN PATENT DOCUMENTS

0159627 10/1985 European Pat. Off. .
2215178 8/1974 France .

Primary Examiner—Michael W. Ball
Assistant Examiner—Michele K. Yoder
Attorney, Agent, or Firm—Donald M. Sell; Walter N. Kirn; Stephen W. Bauer

[57] ABSTRACT

Apparatus and method for applying heat-sensitive adhesive tape, such as frontal diaper tape, of the type having a layer of heat sensitive adhesive material to a web moving at high speed, such as a web of water-resistant material designed for use as the outer layer of disposable diapers. The apparatus comprises a tape-feed wheel for preheating and feeding the tape to the apparatus from a supply of generally continuous tape, and a tape-applying wheel in rolling engagement with the web for applying tape fed to it from the tape-feed wheel to the web. The tape-applying wheel includes vacuum passageways for providing suction through a circumferential surface of the tape-applying wheel to hold the tape thereon, and a heating mechanism for heating the tape to an elevated temperature at which the heat-sensitive adhesive is tacky and for maintaining the tape at the elevated temperature until it is applied to the web. Successive end portions of the tape are cut against the tape-applying wheel into pieces to be applied to the web, and each successive piece of tape cut from the tape is accelerated by the tape-applying wheel from the relatively slow velocity of the tape-feed wheel to the relatively fast velocity of the web and applied to the web.

24 Claims, 3 Drawing Sheets

APPARATUS AND METHOD FOR APPLYING HEAT-SENSITIVE ADHESIVE TAPE TO A WEB MOVING AT HIGH SPEED

This invention relates generally to apparatus for and methods of applying heat-sensitive adhesive tape to a web moving at high speed, and more particularly such apparatus for and methods of applying frontal diaper tape to a web of water-resistant material designed for use as the outer layer of disposable diapers.

BACKGROUND OF THE INVENTION

Pressure-sensitive adhesive tapes, which have traditionally been applied to moving webs, frequently adhere to adjacent layers of tape on tape-supply reels, making consistent and reliable unwinding difficult. One approach to solving this problem is to use heat-sensitive adhesive tape in lieu of the pressure-sensitive adhesive tape, since they do not adhere to adjacent layers unless heated. The high temperatures required to apply the tape, however, sometimes cause the tape or the web to which the tape is being applied to become overly softened, possibly losing their integrity and stretching or tearing during application of the tape. These problems are particularly aggravating in commercial-production scale apparatus for applying frontal diaper tapes to webs, both of which are relatively thin, because of the desirability of obtaining high production rates without sacrificing quality.

SUMMARY OF THE INVENTION

The present invention provides apparatus for and methods of applying heat-sensitive adhesive tape, such as frontal diaper tape, of the type having a layer of heat sensitive adhesive material that is tacky at an elevated temperature substantially greater than room temperature but not tacky at room temperature to a web moving at high speed, e.g., up to 700 linear-feet per minute (210 m/minute), such as a web of water-resistant material designed for use as the outer layer of disposable diapers; that is adapted to accommodate a web moving at various and changing speeds without over or under heating the tape; and that is designed to prevent, or at least reduce, tearing or distortion of heated tape.

Generally, the apparatus of the invention comprises a tape feed wheel for feeding the tape to the apparatus from a supply of generally continuous tape, and a tape-applying wheel in rolling engagement with the web for applying tape fed to tape-applying wheel from the tape feed wheel to the web. Preheating means is provided for heating the tape along the tape-feed wheel to a tape-feed temperature at which the heat-sensitive adhesive layer is tacky or substantially softened. The tape-feed wheel is adapted to rotate at a feed velocity appropriate for feeding a sufficient quantity of tape to the apparatus for application to the web.

The tape-applying wheel includes a generally cylindrical or circumferential surface having sufficiently low friction for sliding engagement with the tape such that the tape is substantially undistorted and untorn by the sliding engagement. The tape-applying wheel is adapted to rotate at a tape-applying velocity greater than the feed velocity and with a circumferential surface velocity substantially equal to the speed of the web. The apparatus includes vacuum means for providing suction through the circumferential surface of the tape-applying wheel to hold the tape thereon, and heating means for heating the tape along the tape-applying wheel to the elevated temperature at which the heat-sensitive adhesive is tacky and for maintaining the tape at the elevated temperature until it is applied to the web.

Cutting means is provided for cutting successive end portions of the tape in sliding engagement with the tape-applying wheel into pieces to be applied to the web. The cutting means is actuated in response to the rotary position of the tape-applying wheel. Buffing means is provided adjacent a surface of the web opposite the tape-applying wheel for pressing the web and the piece of tape to be applied to the web together between the buffing means and tape-applying wheel so that the piece of tape adheres to the web.

The vacuum means is adapted to hold tape fed to the tape-applying wheel in sliding engagement with the circumferential surface of the tape-applying wheel with the tape moving at the tape-feed velocity until it is cut, and the tape-applying wheel is adapted to accelerate each successive piece of tape cut from the successive end portions of the tape from the tape-feed velocity to the tape-applying velocity substantially equal to the velocity of the web so that the tape and web are moving at substantially equal velocity when the tape is applied to the web.

The method of this invention generally comprises the steps of maintaining a peripheral, e.g., circumferential or cylindrical, surface of the tape-applying wheel in rolling engagement with the web and rotating the tape-applying wheel at a tape-applying velocity where the velocity of the peripheral surface of the tape-applying wheel is substantially equal to the speed of the web. The tape is fed along the tape-feed wheel to the tape-applying wheel from a supply of generally continuous tape at a tape-feed velocity lower than the tape-applying velocity and appropriate for feeding a sufficient quantity of tape for application to the web, and the tape is preheated along the tape-feed wheel to a tape-feed temperature at which the heat-sensitive adhesive layer is tacky or substantially softened. Suction is provided through a portion of the peripheral surface of the tape-applying wheel to hold the tape thereon, and the peripheral surface of the tape-applying wheel is heated to heat the tape substantially to the elevated temperature at which the heat-sensitive adhesive is generally tacky and for maintaining the tape substantially at the elevated temperature until it is applied to the web.

The portion of the tape to be cut is maintained in generally low-friction sliding engagement with the peripheral surface of the tape-applying wheel such that the tape is substantially undistorted and untorn by the sliding engagement and with the tape moving at the tape-feed velocity until it is cut. Successive end portions of the tape are cut against the tape-applying wheel into pieces to be applied to the web in response to the rotary position of the tape-applying wheel. Each successive piece of tape cut from the successive end portions is accelerated from the tape-feed velocity to the tape-applying velocity substantially equal to the velocity of the web so that the tape and web are moving at substantially equal velocity when the tape is applied to the web. The web and the piece of tape to be applied to the web are pressed together between the buffing means and the tape-applying wheel so that the piece of tape adheres to the web.

Other features will be in part apparent and in part pointed out hereinafter.

BRIEF DESCRIPTION OF THE DRAWINGS

The present invention will be further described with reference to the drawings wherein corresponding reference characters indicate corresponding parts throughout the several views of the drawings, and wherein.

DETAILED DESCRIPTION

Figure 1:
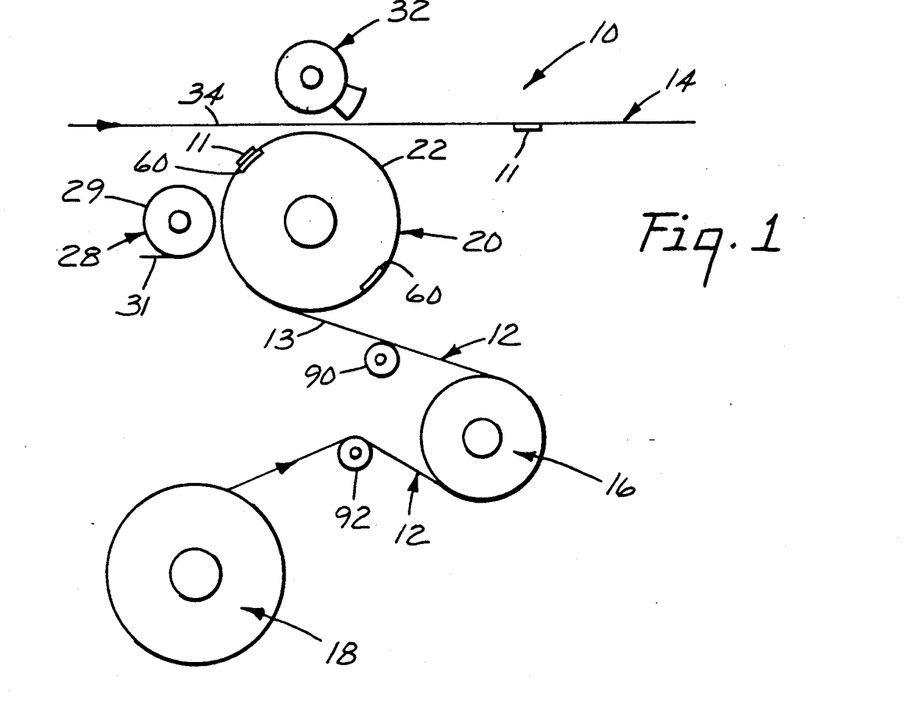
FIG. 1 is a schematic view of an apparatus of the present invention.

Now referring to the drawings, and particularly to FIG. 1, apparatus of the present invention is designated in its entirety by the reference numeral 10. The apparatus 10 is designed for applying pieces 11 of heat-sensitive adhesive tape 12 to a web 14 moving at high speed in spaced relationship along the web. The tape 12 is of the type having a layer 13 of heat-sensitive adhesive material that is generally tacky at an elevated temperature substantially greater than room temperature but substantially not tacky at room temperature. For example, such tape 12 may include the frontal diaper tape described in coassigned U.S. Pat. No. 4,710,190 (which is incorporated herein by reference), and specifically designed to be applied to a web of water-resistant material (e.g., polyethylene) used as the outer layer of disposable diapers. The frontal diaper tape 12 provides a reinforced area for receiving pressure-sensitive adhesive tape of the type used by the consumer to fasten the diaper. Alternatively, the tape 12 being applied may include one portion of a mechanical fastening device, such as either the "hook" or "loop" portion of the hook and loop means sold under the trademark Scotchmate by Minnesota Mining and Manufacturing Co. of St. Paul, MN, so that the consumer may releasably fasten the diaper by applying the other portion of such a fastening device to the tape. Other types of tape 12 having a heat-sensitive adhesive layer 13 may also be applied with the apparatus 10.

The apparatus 10 generally comprises a tape-feed wheel generally designated 16 for feeding the tape 12 to the apparatus from a supply of generally continuous tape, such as tape-supply reel 18, and a tape-applying wheel generally designated 20 in rolling engagement with the web 14 for applying tape fed to it from the tape-feed wheel to the web. As used herein, "rolling engagement" includes maintaining the web in traction on the wheel and maintaining contact between a web and wheel moving in the same direction at generally similar velocities without the web actually being in traction on the wheel. Preheating means (e.g., hot oil circulating through the tape-feed wheel 16 at approximately 94 degrees Centigrade) is provided for heating the tape-feed wheel to heat the tape 12 to a tape-feed temperature at which the heat-sensitive adhesive layer 13 is tacky or preferably merely substantially softened. The tape-feed wheel 16 is adapted to rotate at a tape-feed velocity appropriate for feeding a sufficient quantity of tape to the apparatus for application to the web.

The tape-applying wheel 20 includes a peripheral or preferably generally circumferential surface 22 having sufficiently low friction for sliding engagement with the tape 12 such that the tape is substantially undistorted and untorn by the sliding engagement. The tape-applying wheel 20 is adapted to rotate at a tape-applying velocity greater than the feed velocity of the tape-feed wheel 16 (e.g., at an approximately nine-to-one velocity ratio) and with a circumferential surface 22 velocity substantially equal to the speed of the web 14. Vacuum means (e.g., passageways 24 and ducts 26 shown in FIGS. 2 and 3) provide suction through the circumferential surface 22 of the tape-applying wheel 20 to hold the tape 12 thereon, and heating means (e.g., hot oil circulating through the tape-applying wheel) heat the tape-applying wheel 20 to heat the tape 12 to the elevated temperature at which the heat-sensitive adhesive 13 is tacky and for maintaining the tape at the elevated temperature until it is applied to the web 14.

As shown in FIG. 1, cutting means generally designated 28 is provided for cutting successive end portions of the tape 12 in sliding engagement with the tape-applying wheel 20 into pieces to be applied to the web 14, such as piece 11 shown as already adhered to the web. The cutting means 28 is actuated in response to the rotary position of the tape-applying wheel to ensure that a piece of tape 12 is available at the appropriate time for application to the web 14. For example, the cutting means 28 may comprise a wheel 29 driven at such a velocity that a conventional blade 31 extending outwardly from the wheel 29 strikes tape 12 along the strike plates 60 of the tape-applying wheel to cut the tape into the pieces 11. Buffing means generally designated 32 is provided adjacent a surface 34 of the web 14 opposite the tape-applying wheel 20 for pressing the web and the piece of tape to be applied to the web together between the buffing means and tape-applying wheel so that the piece of tape adheres to the web.

The vacuum means is adapted to hold tape 12 fed to the tape-applying wheel 20 in sliding engagement with the circumferential surface 22 of the tape-applying wheel with the tape moving at the tape-feed velocity until it is cut, and the tape-applying wheel 20 is adapted to accelerate each successive piece of tape 12 cut from the successive end portions of the tape from the tape-feed velocity to the tape-applying velocity substantially equal to the velocity of the web 14 so that the tape and web 14 are moving at substantially equal velocity when the tape is applied to the web.

Figure 3:
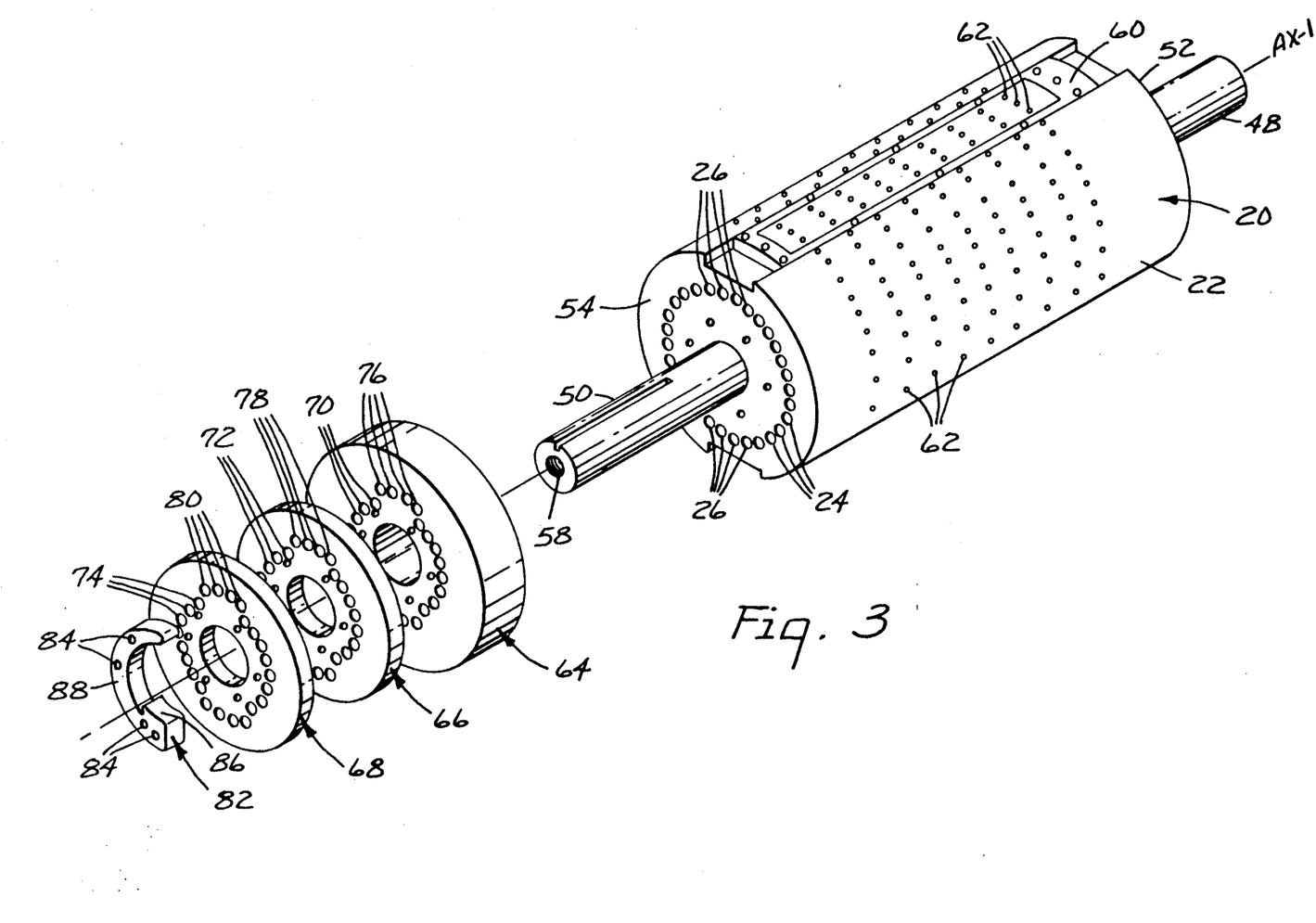
FIG. 3 is an exploded perspective view of the tape-applying wheel of FIG. 2.

As shown in FIG. 3, the tape-applying wheel 20 includes an inner cylindrical part 36 (e.g., of steel material) having an annular recess 38 with a depth extending radially inwardly from the surface of the inner part and a width extending longitudinally along a substantial portion of the surface. An elongate spiraling member 40 (e.g., rod or wire) is provided in the recess 38 of the inner part 36, and extends substantially throughout the width of the recess and has a diameter or thickness substantially equal to the depth of the recess. An outer annular part 42 of steel material has an internal bore 44 closely receiving the inner part 36 and contacting the spiraling member 40 to form a spiraling passageway 46 in the recess along the spiraling member for circulating heated oil through the tape-applying wheel 20. Walls defining the spiraling passageway 46 are formed by the internal bore 44 of the outer part 42, the spiraling member 40 and the inner or bottom surface of the recess 38 of the inner part 36. The passageway 46 spirals substantially longitudinally substantially through the tape-applying wheel 20 generally near the circumferential surface of the wheel. Axle portions 48, 50 extend longitudinally outwardly from opposite ends 52, 54 of the inner part 36 of the wheel 20 for rotatably supporting the wheel on conventional bearings (not shown). The axle portions 48, 50 have coaxial bores 56, 58 communicating with the passageway 36 for feeding heated oil to the passageway and removing oil therefrom.

The spiraling passageway 46, coaxial bores 56, 58, along with a conventional source of heated oil (not shown) and the heated oil or other suitable fluid, constitute heating means for heating the peripheral surface 22 of the tape-applying wheel 20. Alternative heating means include electrical heating elements formed in the tape-applying wheel or any other suitable heating means, although heated oil or fluid is preferred, since it is believed that localized hot spots are less likely to form on the peripheral surface with this type of heating mechanism, and since the temperature of the oil can be readily ascertained and controlled.

The preheating means of the tape-feed wheel 16 also includes a spiraling passageway (not shown) similar to the passageway 36 of the tape-applying wheel 20, and coaxial bores (not shown) extending through axle portions of the wheel for circulating heated oil through the wheel. The passageway of the tape-feed wheel 16 preferably communicates with the passageway 36 and bores 56, 58 of the tape-applying wheel 20 to supply heated oil to the tape-applying wheel. Although the oil may be circulated through the wheels 16 and 20 in either direction, it is preferably circulated through the tape-feed wheel 16 first and then through the tape-applying wheel 20, since there is greater heat loss through the tape-feed wheel than through the tape-applying wheel.

The tape-applying wheel 20 preferably includes two hardened-steel strike plates 60 (FIG. 3) extending longitudinally along the circumferential surface 22 of the wheel on opposite sides of the wheel. The strike plates 60 have curved outer surfaces against which the cutting means 28 cuts the tape 12. The outer surfaces of the strike plates 60 define an arc with a radius about the central longitudinal axis AX-1 of the tape-applying wheel 20, and form two portions of the circumferential surface 22 of the tape-applying wheel.

A multitude of tiny cavities or pits are formed in the cylindrical surface 22 of the tape-applying wheel 20 by electrical-discharge machining (EDM) until a surface roughness of approximately 400 microinches rms (10 micrometers rms) is obtained. The pitted cylindrical surface 22 of the wheel is polished while the wheel is turning with a fine emery cloth to form smooth plateaus covering approximately 40 percent of the surface. Electroless nickel is then deposited on the surface as a binding layer, and industrial hard chrome is deposited on the nickel-treated surface to form a generally low-friction surface along which the tape 12 can slide without excessive distortion or tearing. The tape-feed wheel 16 may have a similar surface treatment, or preferably is plasma coated with tungsten carbide to obtain a surface having a hardness of approximately 72 on the Rockwell C scale.

Figure 2:
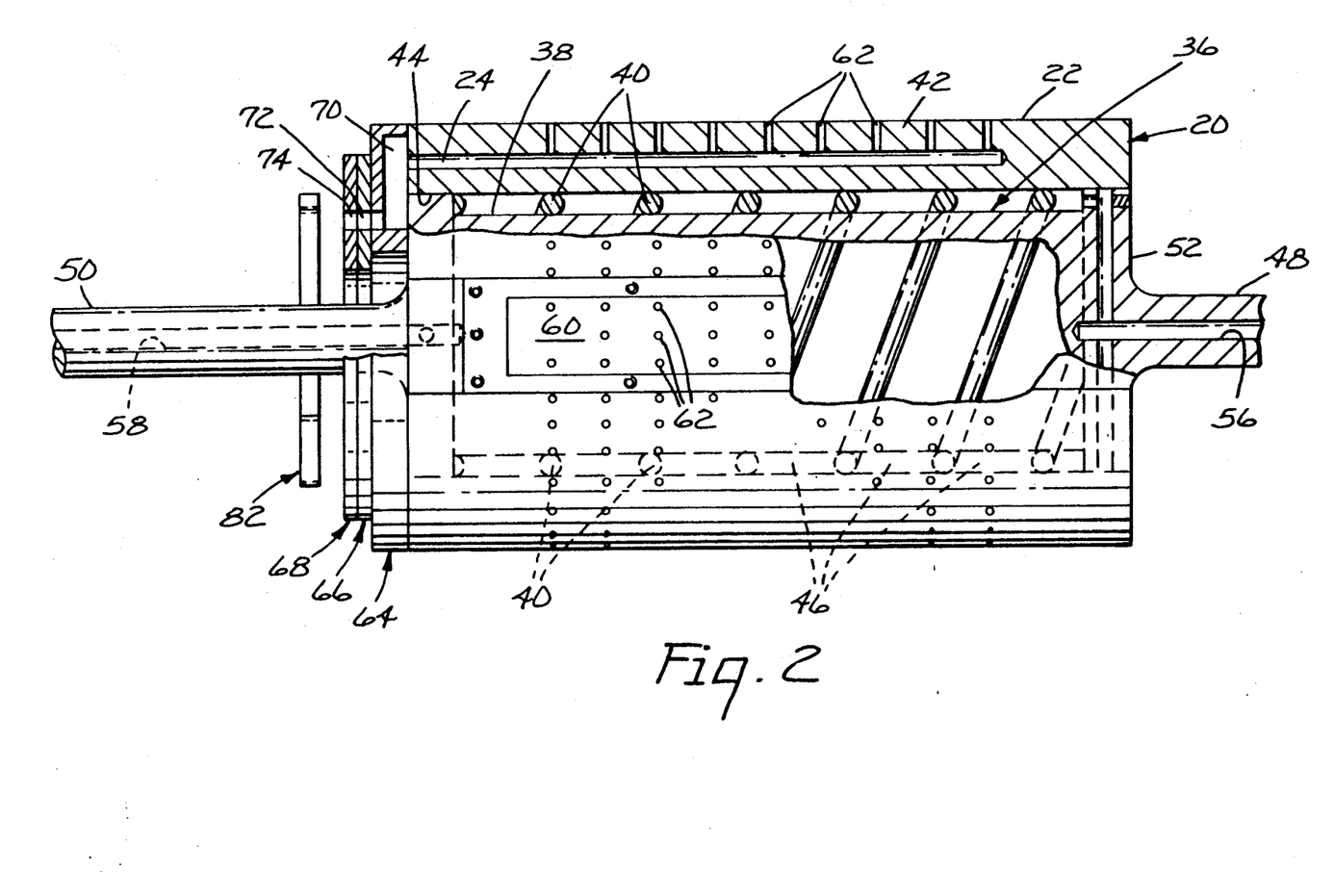
FIG. 2 is an enlarged side view of a tape-applying wheel of the apparatus of FIG. 1, partially broken away to illustrate details.

The vacuum means includes walls in the outer part 42 of the tape-applying wheel 20 forming a plurality of spaced vacuum passageways 24 generally adjacent the surface 22 of the wheel extending longitudinally of the wheel from one end, e.g., the left end 54 in FIGS. 2 and 3, of the wheel, and vacuum ducts (not shown) in the strike plates 60 extending longitudinally of the tape-applying wheel from the left end 54 of the wheel and communicating with vacuum ducts 26 in the outer part of the wheel. Each vacuum passageway 24 and duct has a plurality of spaced openings 62 communicating with the cylindrical surface 60 or the outer surface of the strike plate 60 for providing suction through the surfaces to hold the tape 12 or a piece 11 of tape cut from the tape on the surface.

An aluminum adapter manifold 64, insulating plate 66 of fused-diatomacous earth and stainless-steel end plate 68 may be provided on the left end 54 of the tape-applying wheel 20 with the insulating plate separating or "sandwiched" between the end plate from the adapter manifold and wheel to thermally isolate the end plate from the heated wheel in order to reduce wear on the end plate. The adapter manifold 64, insulating plate 66 and end plate 68 have a plurality of vacuum passageways 70, 72 and 74, respectively, and ducts 76, 78, 80, respectively, communicating with corresponding passageways 24 and ducts 26 of the tape-applying wheel 20.

A stationary vacuum manifold 82 is provided (e.g., mounted on a stationary frame (not shown)) adjacent the left end 54 of the tape-applying wheel 20. The vacuum manifold 82 is generally crescent shaped with an arc substantially about the axis AX-1 of rotation of the tape-applying wheel 20, and is maintained in sealing-sliding engagement with the end plate 68 of the wheel for selectively applying vacuum to the vacuum passageways 24 and ducts 26 of the wheel via the passageways and ducts of the end plate 68, insulating plate 66 and adapter manifold 64. The vacuum manifold 82 includes a plurality of openings 84 communicating with a cavity (not shown) formed in the side of the manifold that is engaging the end plate 68 for supplying vacuum to the tape-applying wheel 20.

The vacuum manifold 82, and the vacuum passageways and vacuum ducts are arranged and configured such that suction is applied only to portions of the circumferential surface 22 of the tape-applying wheel 20 and outer surface of the strike plate 60 that are engaging the tape 12 or a piece 11 of tape cut from a successive end portion of the tape. For example, the vacuum passageways 70 of the adapter manifold 64 open through the outer (left in FIG. 3) side of the adapter manifold substantially equally spaced generally along a circle coaxial with the tape-applying wheel 20, and the ducts 76 of the adapter manifold open through the outer side of the adapter manifold along arcs coaxial with the circle formed by passageways 70 and spaced radially outwardly of the circle. The passageways 72, 74 and ducts 78, 80 of the insulating plate 66 and end plate 68 are arranged along substantially identical circles and arcs coaxial with the tape-applying wheel 20 so that the arcs formed by the ducts 80 of the end plate are disposed radially outwardly relative to the circle formed by the passageways 74 of the end plate.

The center line of the arc of the vacuum manifold 82 has a radius substantially equal to the radius of the arc formed by ducts 80 of the end plate 68 so that vacuum is supplied to any ducts 80, 78, 76 and 26 registering with the vacuum manifold throughout substantially the entire length along the arc of the vacuum manifold to provide vacuum to the outer surface of the strike plate 60. The vacuum manifold includes an enlarged section 86 extending radially inwardly from the arc of the manifold toward the central axis AX-1 forming a portion of the cavity of the manifold for providing vacuum to the passageways 74, 72, 70 and 24 and providing suction along a portion of the surface 22 of the tape-applying wheel. The arcuate section 88 of the vacuum manifold 82 is thus adapted for providing suction to hold each successive piece 11 of tape 12 cut from a successive end portion of the tape on the strike plate 60, and the enlarged section 86 is adapted for providing suction to hold the uncut portion of tape 12 in sliding engagement with the circumferential surface of the tape-applying wheel, it being observed that the vacuum manifold does not provide vacuum to those vacuum passageways and ducts that are not engaging the tape or a piece of tape cut from a successive end portion of the tape. As the tape-applying wheel 20 rotates the vacuum passageways and ducts move relative to the vacuum manifold 82 so that vacuum is provided only to the appropriate portions of the outer surfaces of the tape-applying wheel and strike plate 60.

An idler roller 92 may be provided for positioning and tensioning the tape 12 supplied to the tape-feed wheel 16 relative to the tape-feed wheel. A tape-lift wheel 90 may be provided generally between the tape-feed wheel 16 and the tape-applying wheel 20. The tape-lift wheel 90 is positioned to engage the tape 12 when it departs from a generally direct tangential path between the tape-feed wheel and tape-applying wheel (i.e., the path of the tape in FIG. 1) to move or return the tape to the generally direct tangential path, thereby preventing fouling or entangling of the tape between the tape-feed and tape-applying wheels. The tape-lift wheel 90 may have a low-friction surface treatment similar to that given to the tape-applying wheel 20, and is preferably rotated with a tangential surface velocity approximately three percent greater than the tape-feed velocity of the tape-feed wheel 16.

In operation, the peripheral or circumferential surface 22 of the tape-applying wheel 20 is maintained in rolling engagement with the web 14 and rotated at a tape-applying velocity where the velocity of the peripheral surface of the tape-applying wheel is substantially equal to the speed of the web. The tape 12 is feed along the tape-feed wheel 16 with the heat-sensitive adhesive layer 13 facing the tape-feed wheel to the tape-applying wheel with the heat-sensitive adhesive layer facing away from the tape-applying wheel from a tape-supply reel 18, the tape-feed wheel rotating at a tape-feed velocity lower than the tape-applying velocity and appropriate for feeding a sufficient quantity of tape for application to the web. The tape 12 along the tape-feed wheel 16 is preheated to the tape-feed temperature at which the heat-sensitive adhesive layer is tacky or substantially softened. Suction is provided through a portion of the peripheral surface 22 of the tape-applying wheel 20 to hold the tape 12 thereon, and the peripheral surface of the tape-applying wheel is heated to heat the tape substantially to the elevated temperature at which the heat-sensitive adhesive is generally tacky and for maintaining the tape substantially at the elevated temperature until it is applied to the web.

The portion of the tape 12 to be cut is maintained in generally low-friction sliding engagement with the peripheral surface 22 of the tape-applying wheel 20 such that the tape is substantially undistorted and untorn by the sliding engagement and with the tape moving at the tape-feed velocity until it is cut. Successive end portions of the tape 12 are cut against the strike plates 60 of the tape-applying wheel 20 into pieces 11 to be applied to the web. Each successive piece 11 of tape 12 cut from the successive end portions of the tape is accelerated along the tape-applying wheel 20 from the tape-feed velocity to the tape-applying velocity substantially equal to the velocity of the web so that the tape and web are moving at substantially equal velocity when the tape is applied to the web. The web 14 and the accelerated piece 11 of tape 12 are pressed together between a buffing means 32 and the tape-applying wheel 20 so that the piece of tape adheres to the web.

Figure 4:
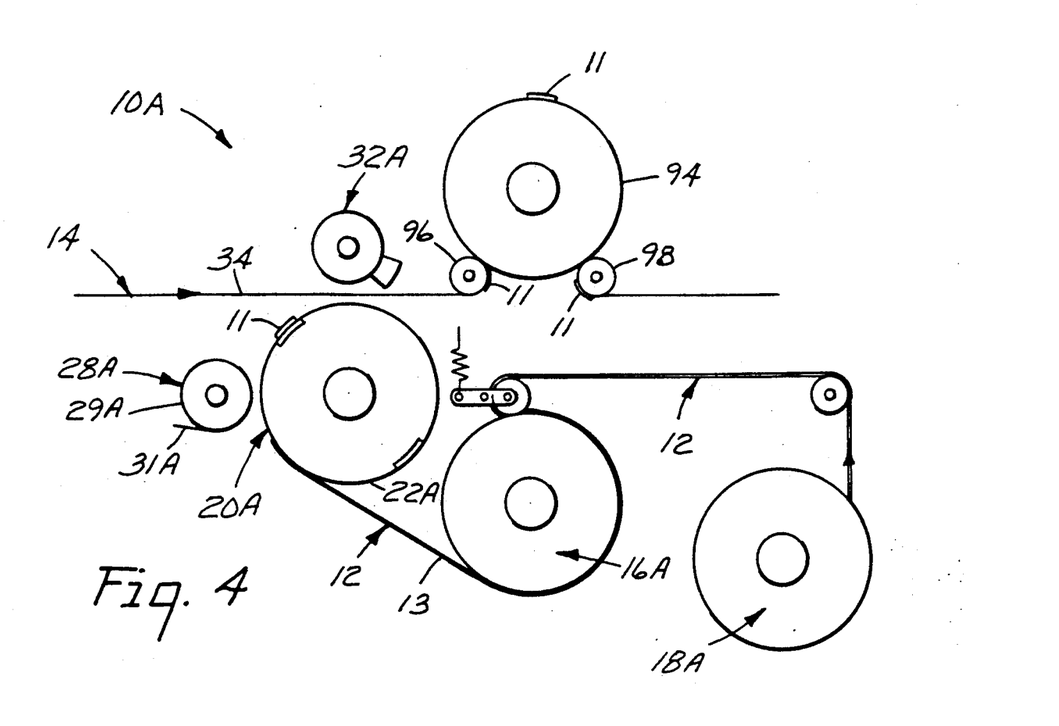
FIG. 4 is a schematic view similar to FIG. 1, illustrating another embodiment of the apparatus of this invention.

FIG. 4 illustrates a second embodiment of the invention wherein the tape-feed 16A and tape-applying wheel 20A are so positioned relative to one another and rotate in such directions that the tape 12 rides along the tape-feed and tape-applying wheels with the heat-sensitive adhesive layer 13 facing away from both the tape-feed and tape-applying wheels. Reference characters ending with an "A" in FIG. 4 designate parts or features similar to those illustrated in the other figures having the same reference numerals not ending with an "A". The heating means for heating the tape-applying wheel 20A is adapted for heating the heat-sensitive adhesive layer 13 of the tape 12 to such an elevated temperature that the tape at least temporarily adheres to the web 14.

The apparatus 10A includes a post-heat wheel 94 having a peripheral surface along which the web rides after the pieces 11 of tape 12 are applied to the web 14 for additional heating of the tape. Two idler rollers 96 and 98 are positioned for wrapping the web 14 substantially around the peripheral surface of the post-heat wheel 94. Post-heating means similar to the heating and preheating means of the tape-applying and tape-feed wheels 20, 20A and 16, 16A is provided for heating the peripheral surface of the post-heat wheel 94 (e.g., to a temperature of approximately 175-200 F. (80-94 C.)) to heat the heat-sensitive adhesive layer 13 of the pieces 11 of tape 12 to a temperature above the elevated temperature but below the melting temperature of the web to form a permanent bond between the pieces of tape and the web.

As various changes could be made in the constructions and methods described above without departing from the scope of the invention, it is intended that all matter contained in the description above or shown in the accompanying drawings shall be interpreted as illustrative and not in a limiting sense.

What is claimed is:

1. Apparatus for applying pieces of heat-sensitive adhesive tape, such as frontal diaper tape, of the type having a layer of heat sensitive adhesive material that is generally tacky at an elevated temperature substantially greater than room temperature but substantially not tacky at room temperature to a web moving at high speed, such as a web of water-resistant material designed for use as the outer layer of disposable diapers, the pieces of tape being applied in spaced relationship along the web), the apparatus comprising:

a tape feed wheel for feeding the tape to the apparatus from a supply of generally continuous tape, the tape feed wheel being adapted to rotate at a feed velocity appropriate for feeding a sufficient quantity of tape to the apparatus for application to the web;

preheating means for heating a tape-feed wheel to heat the tape to a tape-feed temperature at which the heat-sensitive adhesive layer is tacky or substantially softened;

a tape-applying wheel in rolling engagement with the web for applying tape fed to it from the tape feed wheel to the web, the tape-applying wheel including a generally circumferential surface having sufficiently low friction for sliding engagement with the tape such that the tape is substantially undistorted and untorn by the sliding engagement, the tape-applying wheel being adapted to rotate at a tape-applying velocity greater than the feed velocity and with a circumferential surface velocity substantially equal to the speed of the web;

vacuum means for providing suction through the circumferential surface of the tape-applying wheel to hold the tape thereon;

heating means for heating the circumferential surface of the tape-applying wheel to heat the tape to the elevated temperature at which the heat-sensitive adhesive is generally tacky and for maintaining the tape at the elevated temperature until it is applied to the web;

cutting means for cutting successive end portions of the tape in sliding engagement with the tape-applying wheel into pieces to be applied to the web, the cutting means being actuated in response to the rotary position of the tape-applying wheel; and buffing means adjacent a surface of the web opposite the tape-applying wheel for pressing the web and the piece of tape to be applied to the web together between the buffing means and tape-applying wheel so that the piece of tape adheres to the web;

the vacuum means being adapted to hold tape fed to the tape-applying wheel in sliding engagement with the circumferential surface of the tape-applying wheel with the tape moving at the tape-feed velocity until it is cut, and the tape-applying wheel being adapted to accelerate each successive piece of tape cut from the successive end portion of the tape from the tape-feed velocity to the tape-applying velocity substantially equal to the velocity of the web so that the tape and web are moving at substantially equal velocity when the tape is applied to the web.

2. Apparatus according to claim 1 wherein the heating means for heating the tape-applying wheel includes walls in the tape-applying wheel forming a passageway for heated oil to flow through to heat the tape-applying wheel to the elevated temperature at which the heat-sensitive adhesive is tacky, the passageway spiraling substantially longitudinally substantially through the tape-applying wheel generally near the circumferential surface of the wheel, the tape-applying wheel having axle portions extending longitudinally outwardly from opposite ends of the wheel for rotatably supporting the wheel on bearings, the axle portions having coaxial bores communicating with the passageway for feeding heated oil to the passageway and removing oil therefrom.

3. Apparatus according to claim 2 wherein the preheating means for heating the tape-feed wheel includes walls in the tape-feed wheel forming a passageway for heated oil, the passageway of the tape-feed wheel communicating with the passageway and coaxial bores of the tape-applying wheel to supply heated oil to the tape-applying wheel.

4. Apparatus according to claim 2 wherein the tape-applying wheel includes an inner cylindrical part having an annular recess with a depth extending radially inwardly from the surface of the inner part and a width extending longitudinally along a substantial portion of the surface, an elongate spiraling member in the recess extending substantially throughout the width of the recess and having a diameter or thickness substantially equal to the depth of the recess, and an outer annular part having an internal bore closely receiving the inner part and contacting the spiraling member to form the passageway of the tape-applying wheel in the recess along the spiraling member.

5. Apparatus according to claim 1 wherein the vacuum means includes walls in the tape-applying wheel forming a plurality of spaced vacuum passageways generally adjacent the surface of the wheel extending longitudinally of the wheel from one end of the wheel, each vacuum passageway having a plurality of spaced openings communicating with the cylindrical surface of the tape-applying wheel, the apparatus further comprising a stationary vacuum manifold in sealing-sliding engagement with only a portion of the one end of the wheel for applying vacuum only to the vacuum passageways that are adjacent the tape to hold the tape on the tape-applying wheel without applying vacuum to the portions of the circumferential surface of the wheel that are not adjacent the tape.

6. Apparatus according to claim 5 wherein the vacuum manifold consists essentially of a single vacuum manifold that is generally crescent shaped with an arc substantially about the axis of rotation of the tape-applying wheel.

7. Apparatus according to claim 6 wherein the tape-applying wheel includes a strike plate extending longitudinally along the circumferential surface of the wheel and having an outer surface against which the cutting means cuts the tape, the vacuum means having vacuum ducts in the strike plate extending longitudinally of the tape-applying wheel from the one end of the wheel for providing suction through the outer surface of the strike plate for holding a piece of tape cut from a successive end portion of the tape on the strike plate, the vacuum manifold, vacuum passageways and vacuum ducts being arranged such that suction is applied only to portions of the circumferential surface of the tape-applying wheel and outer surface of the strike plate that are engaging the tape or a piece of tape cut from a successive end portion of the tape.

8. Apparatus according to claim 7 wherein the tape-applying wheel is formed of steel and the strike plate is formed of hardened steel, the cylindrical surface of the tape-applying wheel having a multitude of tiny cavities formed therein by electrical-discharge machining, the cylindrical surface and outer surface being polished to form smooth plateaus and having chrome deposited thereon.

9. Apparatus for applying pieces of heat-sensitive adhesive tape, such as frontal diaper tape, of the type having a layer of heat sensitive adhesive material that is generally tacky at an elevated temperature substantially greater than room temperature but substantially not tacky at room temperature to a web moving at high speed, such as a web of water-resistant material designed for use as the outer layer of disposable diapers, the pieces of tape being applied in spaced relationship along the web, the apparatus comprising:

a tape feed wheel for feeding the tape to the apparatus from a supply of generally continuous tape, the tape fed wheel being adapted to rotate at a feed velocity appropriate for feeding a sufficient quantity of tape to the apparatus for application to the web;

preheating means for heating the tape-feed wheel to heat the tape to a tape-feed temperature at which the heat-resensitive adhesive layer is tacky or substantially softened;

a tape-applying wheel in rolling engagement with the web for applying tape fed to it from the tape feed wheel to the web, the tape-applying wheel including a generally circumferential surface having sufficiently low friction for sliding engagement with the tape such that the tape is substantially undistorted and untorn by the sliding engagement, the tape-applying wheel being adapted to rotate at a tape-applying velocity greater than the feed velocity and with a circumferential surface velocity substantially equal to the speed of the web;

vacuum means for providing suction through the circumferential surface of the tape-applying wheel to hold the tape thereon; the vacuum means including walls in the tape-applying wheel forming a plurality of spaced vacuum passageways generally adjacent the surface of the wheel extending longitudinally of the wheel from one end of the wheel, each vacuum passageway having a plurality of spaced openings communicating with the cylindrical surface of the tape-applying wheel;

a stationary vacuum manifold in sealing-sliding engagement with the one end of the tape-applying wheel for applying vacuum to the vacuum passageways that are adjacent the tape to hold the tape on the tape-applying wheel, the vacuum manifold being generally crescent shaped with an arc substantially about the axis of rotation of the tape-applying wheel;

heating means for heating the circumferential surface of the tape-applying wheel to heat the tape to the elevated temperature at which the heat-sensitive adhesive is generally tacky and for maintaining the tape at the elevated temperature unit it is applied to the web;

cutting means for cutting successive end portions of the tape in sliding engagement with the tape-applying wheel into pieces to be applied to the web, the cutting means being actuated in response to the rotary position of the tape-applying wheel; and buffing means adjacent a surface of the web opposite the tape-applying wheel for pressing the web and the piece of tape to be applied to the web together between the buffing means and tape-applying wheel so that the piece of tape adheres to the web;

the vacuum means being adapted to hold tape fed to the tape-applying wheel in sliding engagement with the circumferential surface of the tape-applying wheel with the tape moving at the tape-feed velocity until it is cut, and the tape-applying wheel being adapted to accelerate each successive piece of tape cut from a successive end portion of the tape from the tape-feed velocity to the tape-applying velocity substantially equal to the velocity of the web so that the tape and web are moving at substantially equal velocity when the tape is applied to the web;

the tape-applying wheel including a strike plate extending longitudinally along the circumferential surface of the tape-applying wheel and having an outer surface against which the cutting means cuts the tape, the vacuum means having vacuum ducts in the strike plate extending longitudinally of the tape-applying wheel from the one end of the wheel for providing suction through the outer surface of the strike plate for holding a piece of tape-cut from a successive end portion of the tape on the strike plate, the vacuum manifold, vacuum passageways and vacuum ducts being arranged such that suction is applied only to portions of the circumferential surface of the tape-applying wheel and outer surface of the strike plate that are engaging the tape or a piece of tape cut from a successive end portion of the tape;

the tape-applying wheel further including an insulating plate mounted on the wheel adjacent the one end of the wheel and an end plate mounted on the wheel adjacent the insulating plate and sandwiching the insulating plate between it and the wheel, the end plate being in sealing-sliding engagement with the vacuum manifold, and the insulating and end plates having vacuum passageways and ducts registering with the corresponding vacuum passageways and ducts of the tape-applying wheel.

10. Apparatus according to claim 9 wherein the tape-applying wheel further includes an adapter manifold between the insulating plate and the wheel and having inner and outer sides adjacent the wheel and insulating plate, the adapter manifold having a plurality of passageways and ducts registering with respective vacuum passageways and ducts of the tape-applying wheel and insulating plate, the passageways of the adapter manifold opening through the outer side of the adapter manifold spaced generally along a circle coaxial with the wheel and the ducts of the adapter manifold opening through the outer side of the adapter manifold spaced radially outwardly of the circle, the vacuum manifold being configured such that vacuum is applied only to passageways and ducts that apply suction to portions of the circumferential surface of the tape-applying wheel and outer surface of the strike plate that are engaging tape or a piece of tape cut from a successive end portion of the tape.

11. Apparatus according to claim 1 wherein the tape-feed and tape-applying wheels are so positioned relative to one another and rotate in such directions that the tape rides along the tape-feed wheel and tape-applying wheel with the heat-sensitive adhesive layer facing the tape-feed wheel and facing away from the tape-applying wheel, the apparatus further including a tape-lift wheel generally between the tape-fed wheel and the tape-applying wheel, the tape-lift wheel being positioned to engage the tape when it departs from a generally direct tangential path between the tape-feed wheel and tape-applying wheel to move or return the tape to the generally direct tangential path, whereby preventing fouling or entangling of the tape between the tape-feed and tape-applying wheels.

12. Apparatus according to claim 11 further including a tape-supply reel constituting the supply of generally continuous tape for supplying tape to the tape-feed wheel, and an idler roller for positioning and tensioning the tape supplied to the tape-feed wheel relative to the tape-feed wheel.

13. Apparatus according to claim 1 wherein the tape-applying and tape-feed wheels are adapted such that the tape-applying velocity of the tape-applying wheel is approximately at a nine-to-one velocity ratio with respect to the tape-feed velocity of the tape feed wheel.

14. Apparatus according to claim 1 wherein the tape-feed and tape-applying wheel are so positioned relative to one another and rotate in such directions that the tape rides along the tape-feed and tape-applying wheels with the heat-sensitive adhesive layer facing away from the tape-feed and tape-applying wheels.

15. Apparatus according to claim 14 wherein the heating means for heating the tape-applying wheel is adapted for heating the heat-sensitive adhesive layer of the tape to such an elevated temperature that the tape temporarily or permanently adheres to the web, the apparatus further comprising a post-heat wheel having a peripheral surface along which the web rides after the pieces of tape are applied to the web, and post-heating means for heating the peripheral surface of the post-heat wheel to heat the heat-sensitive adhesive layer of the pieces of tape to a temperature above the elevated temperature but below the melting temperature of the web to form a permanent bond between the pieces of tape and the web.

16. Apparatus according to claim 1 wherein the heating means for heating the tape-applying wheel is adapted for heating the heat-sensitive adhesive layer of the tape to such an elevated temperature that the tape temporarily or permanently adheres to the web, the apparatus further comprising a post-heat wheel having a peripheral surface along which the web rides after the pieces of tape are applied to the web, and post-heating means for heating the peripheral surface of the post-heat wheel to heat the heat-sensitive adhesive layer of the pieces of tape to a temperature above the elevated temperature but below the temperature at which the web readily becomes distorted to form a permanent bond between the pieces of tape and the web.

17. A method of applying pieces of heat-sensitive adhesive tape, such as frontal diaper tape, of the type having a layer of heat sensitive adhesive material that is generally tacky at an elevated temperature substantially greater than room temperature but substantially not tacky at room temperature to a web moving at high speed, such as a web of water-resistant material designed for use as the outer layer of disposable diapers, the pieces being applied in spaced relationship along the web, the method comprising the following steps:

maintaining a peripheral surface of a tape-applying wheel in rolling engagement with the web and rotating the tape-applying wheel at a tape-applying velocity where the velocity of the peripheral surface of the tape-applying wheel is substantially equal to the speed of the web;

feeding the tape along a tape-feed wheel to the tape-applying wheel from a supply of generally continuous tape at a tape-feed velocity lower than the tape-applying velocity and appropriate for feeding a sufficient quantity of tape for application to the web;

preheating the tape along the tape-feed wheel to a tape-feed temperature at which the heat-sensitive adhesive layer is tacky or substantially softened;

providing suction through a portion of the peripheral surface of the tape-applying wheel to hold the tape thereon;

heating the peripheral surface of the tape-applying wheel to heat the tape substantially to the elevated temperature at which the heat-sensitive adhesive is generally tacky and for maintaining the tape substantially at the elevated temperature until it is applied to the web;

cutting successive end portions of the tape against the tape-applying wheel into pieces to be applied to the web in response to the rotary position of the tape-applying wheel;

maintaining the portion of the tape to be cut in generally low-friction sliding engagement with the peripheral surface of the tape-applying wheel such that the tape is substantially undistorted and untorn by the sliding engagement and with the tape moving at the tape-feed velocity until it is cut;

accelerating each successive piece of tape cut from the successive end portions of the tape from the tape-feed velocity to the tape-applying velocity substantially equal to the velocity of the web so that the tape and web are moving at substantially equal velocity when the tape is applied to the web; and pressing the web and the piece of tape to be applied to the web together between a buffing means and the tape-applying wheel so that the piece of tape adheres to the web.

18. A method according to claim 17 wherein the tape-applying and tape-feed wheels have passageways for circulating heated oil through the wheels to heat the wheels and the tape riding thereon, the method further including the step of circulating heated oil through the passageways of the tape-applying and tape-feed wheels to heat the tape riding thereon.

19. A method according to claim 17 further including the following steps:

supplying the tape to the tape-feed wheel from a tape-supply wheel;

providing an idler roller generally between the tape-feed wheel and tape-supply wheel;

positioning and tensioning the tape supplied to the tape-feed wheel relative to the tape-feed wheel on the idler roller;

providing and positioning a tape-lift wheel generally between the tape-feed wheel and the tape-applying wheel; and engaging the tape with the tape-lift wheel when the tape departs from a generally direct tangential path between the tape-feed wheel and tape-applying wheel to move or return the tape to the generally direct tangential path, thereby preventing fouling or entangling of the tape between the tape-feed and tape-applying wheels.

20. A method according to claim 17 further including the step of maintaining the tape-applying wheel and tape-feed wheel approximately at a nine-to-one rotational velocity ratio.

21. A method according to claim 17 further including the following steps:

positioning the tape-feed and tape-applying wheels relative to one another and rotating them in such directions that the tape is able to ride along the tape-feed and tape-applying wheels with the heat-sensitive adhesive layer facing away from the tape-feed and tape-applying wheels;

supplying the tape to the tape-feed wheel with the heat sensitive-adhesive layer facing away from the tape-feed wheel; and feeding the tape to the tape-applying wheel from the tape-feed wheel with the heat-sensitive adhesive layer facing away from the tape-applying wheel.

22. A method according to claim 21 further including the following steps:

providing a post-heat wheel having a peripheral surface along which the web rides after the pieces of tape are applied to the web;

running the web after the pieces of tape are applied to the web substantially along the peripheral surface of the post-heat wheel; and heating the peripheral surface of the post-heat wheel to heat the heat-sensitive adhesive layer of the pieces of tape to a temperature above the elevated temperature at which the heat-sensitive material is generally tacky but below the melting temperature of the web to form a permanent bond between the pieces of tape and the web.

23. A method according to claim 17 further including the following steps:

provi­ding a post-heat wheel having a peripheral surface along which the web rides after the pieces of tape are applied to the web;

running the web after the pieces of tape are applied to the web substantially along the peripheral surface of the post-heat wheel; and heating the peripheral surface of the post-heat wheel to heat the heat-sensitive adhesive layer of the pieces of tape to a temperature above the elevated temperature at which the heat-sensitive material is generally tacky but below the melting temperature of the web to form a permanent bond between the pieces of tape and the web.

24. Apparatus according to claim 1 wherein the vacuum means includes walls in the tape-applying wheel forming a plurality of spaced vacuum passageways and ducts generally adjacent the surface of the tape-applying wheel extending longitudinally of the wheel from one end of the wheel, each vacuum passageway and each duct having a plurality of spaced openings communicating with the cylindrical surface of the tape-applying wheel, the vacuum passageways opening through the one end of the tape-applying wheel spaced generally along a circle coaxial with the wheel, and the ducts opening through the one end of the tape-applying wheel spaced radially outwardly of the circle, the apparatus further comprising a stationary vacuum manifold in sealing-sliding engagement with the one end of the wheel for applying vacuum to the vacuum passageways and ducts that are adjacent the tape to hold the tape on the tape-applying wheel, the vacuum manifold being configured such that vacuum is applied only to passageways that apply suction to portions of the circumferential surface of the tape-applying wheel that are engaging tape, and only to ducts that apply suction to portions of the circumferential surface that are engaging tape or a piece of tape cut from a successive end portion of the tape.

* * * * *

UNITED STATES PATENT AND TRADEMARK OFFICE
CERTIFICATE OF CORRECTION

PATENT NO. : 5,021,111
DATED : June 4, 1991
INVENTOR(S) : Douglas A. Swenson It is certified that error appears in the above-identified patent and that said Letters Patent is hereby corrected as shown below:

Col. 3, line 40, "Scotchmate" should read --"Scotchmate"--.

Col. 8, line 54, "web)," should read --web,--.

Col. 10, line 63, "fed" should read --feed--.

Col. 11, line 1, "heat-resensitive" should read --heat-sensitive--

Col. 11, line 36, "unit" should read --until--.

Col. 12, line 45, "tape-fed" should read --tape-feed--.

Signed and Sealed this

Seventeenth Day of August, 1993

Attest:

BRUCE LEHMAN

Attesting Officer

Commissioner of Patents and Trademarks